(12) United States Patent
Kim

(10) Patent No.: US 6,629,615 B2
(45) Date of Patent: *Oct. 7, 2003

(54) ORGANIZER APPARATUS FOR MEDICAL INSTRUMENTS

(76) Inventor: Andrew Kim, 30213 Del Rey Rd., Temecula, CA (US) 92591

( * ) Notice: Subject to any disclaimer, the term of this patent is extended or adjusted under 35 U.S.C. 154(b) by 16 days.

This patent is subject to a terminal disclaimer.

(21) Appl. No.: 09/894,741

(22) Filed: Jun. 27, 2001

(65) Prior Publication Data

US 2002/0092816 A1 Jul. 18, 2002

Related U.S. Application Data

(63) Continuation-in-part of application No. 09/470,081, filed on Dec. 22, 1999, now Pat. No. 6,345,873.

(51) Int. Cl.⁷ ............................................. A47F 7/00
(52) U.S. Cl. .................. 211/85.13; 312/209; 312/223.6
(58) Field of Search ..................... 211/85.13, 85.5; 439/532, 713, 404; 312/209, 223.6

(56) References Cited

U.S. PATENT DOCUMENTS

| | | | | |
|---|---|---|---|---|
| 3,696,920 A | * | 10/1972 | Lahay | 128/DIG. 26 |
| 4,163,372 A | * | 8/1979 | Frye et al. | 174/175 |
| 4,262,985 A | * | 4/1981 | Muehlhausen II | 439/401 |
| 4,457,080 A | * | 7/1984 | Glan | 33/404 |
| 5,312,270 A | * | 5/1994 | Siemon et al. | 439/404 |
| 5,352,136 A | * | 10/1994 | Chen | 439/532 |
| RE35,030 E | * | 8/1995 | Siemon et al. | 439/404 |
| 6,027,369 A | * | 2/2000 | Conorich et al. | 439/532 |
| 6,240,857 B1 | * | 6/2001 | Elizer | 108/147.17 |
| 6,340,317 B1 | * | 1/2002 | Lin | 174/60 |
| 6,345,873 B1 | * | 2/2002 | Kim | 248/68.1 |

* cited by examiner

Primary Examiner—Daniel P. Stodola
Assistant Examiner—Khoa Tran
(74) Attorney, Agent, or Firm—Freling Baker

(57) ABSTRACT

An organizing apparatus for medical instruments includes an elongated substantially rigid support member having opposite ends, a releasable attachment member depending downward from each of the opposite ends for detachable attachment to opposite side edges of a substantially planar support surface, and an elongated line holder mounted on a top surface of the support member and having a plurality of resilient holding members defining line receiving and holding areas between adjacent holding members.

20 Claims, 6 Drawing Sheets

ORGANIZER APPARATUS FOR MEDICAL INSTRUMENTS

REFERENCE TO RELATED APPLICATIONS

The present application is a continuation-in-part of application Ser. No. 09/470,081 filed Dec. 22, 1999, now U.S. Pat. No. 6,345,873, entitled "ARTHROSCOPY ORGANIZER SYSTEM"

BACKGROUND OF THE INVENTION

The present invention relates generally to an arthroscopy and pertains particularly to an arthroscopy organization system.

Arthroscopic operations are carried out with several instruments or tools that are connected by lines and cord to light source, power source, suction source etc. Currently, because of operating room layout, these instruments are unwrapped from sterile wrapping and hooked up and tested after the patient is brought into the operating room. The connection of the instruments to power, water, vacuum and other such supply sources are in a non-sterile area of the operating room. The instruments themselves are placed on the only sterile area in the operating room, the patient or operating table. This preparation takes a considerable amount of time while the patient is in the operating room under anesthesia. This preparation is particularly time consuming when problems such as when one or more inoperable instruments are found. The instrument must be replaced, repaired or adjusted in preparation for the operation.

The act of connecting the lines and cords to the light source, power source and the suction canister typically takes about four minutes if there are no problems. If there is any problem with the monitor, the pump or any other machine or instrument, much more time is wasted correcting the problem while the patient is under anesthesia. The cords and lines to the instruments are brought over the patient and are tied to drapes over the patients body. They are usually in disarray and frequently tangled, resulting in time consuming delay in untangling cords and retrieving instrument. There have been cases of patients under anesthesia being burned by the hot instruments placed directly over the patient's abdomen.

In the parent application, a system was disclosed that solved many of the problems pointed out above. However, that system somewhat complicated and expensive.

Accordingly there is a need for a simple and inexpensive apparatus to organize arthroscopic instruments, their lines and cords and to hold the lines, cords instruments in an organized accessible manner off of and away from the patient.

SUMMARY AND OBJECTS OF THE INVENTION

It is the primary object of the present invention to provide a simple and effective system to organize arthroscopic or endoscopic instruments, their lines and cord and to hold the instruments in an organized, convenient and accessible manner.

In accordance with a primary aspect of the present invention an arthroscopy instrument organizing apparatus comprises a support member having a substantially planar support surface, and a line holder mounted on said support member and having resilient holding members defining line receiving and holding areas between adjacent holding members.

BRIEF DESCRIPTION OF THE DRAWINGS

The above and other objects and advantages of the present invention will become apparent from the following description and the accompanying drawings wherein.

DETAILED DESCRIPTION OF THE PREFERRED EMBODIMENTS

Figure 1:
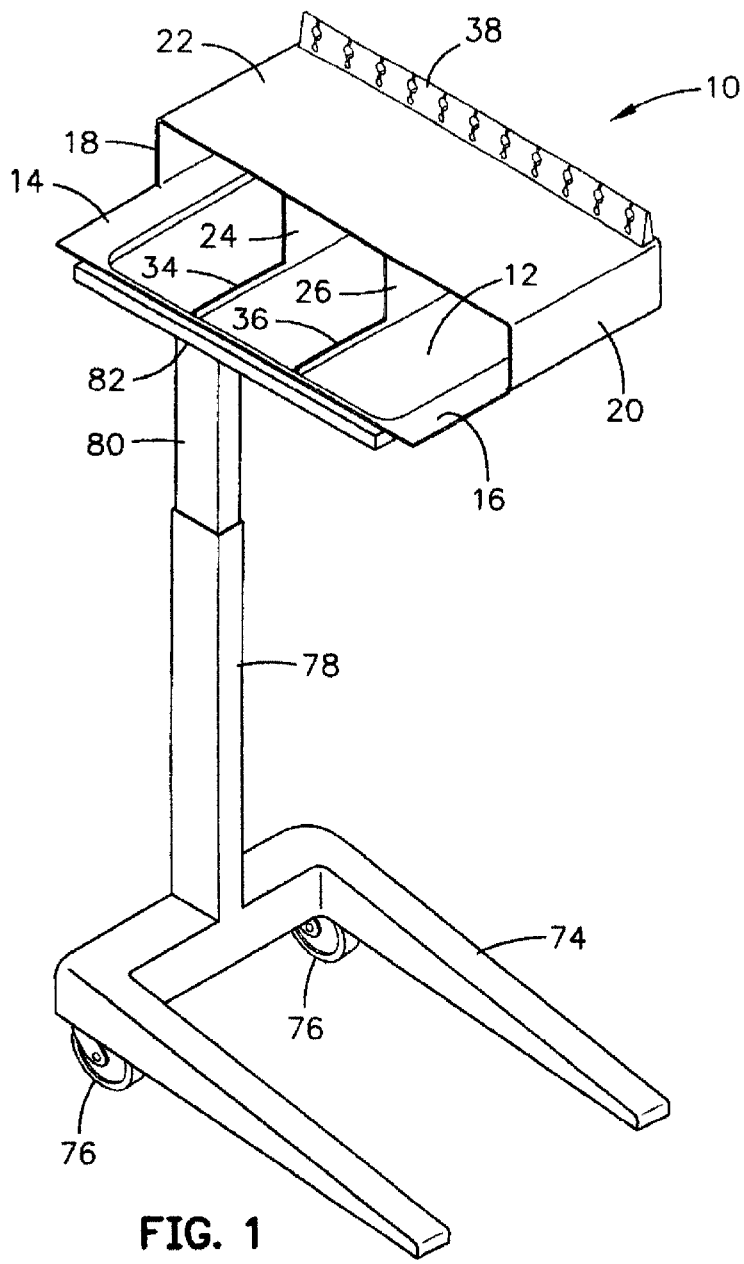
FIG. 1 is a perspective view of an exemplary embodiment of an arthroscopic instrument organizer in accordance with one embodiment of the invention shown mounted on a stand.
Figure 2:
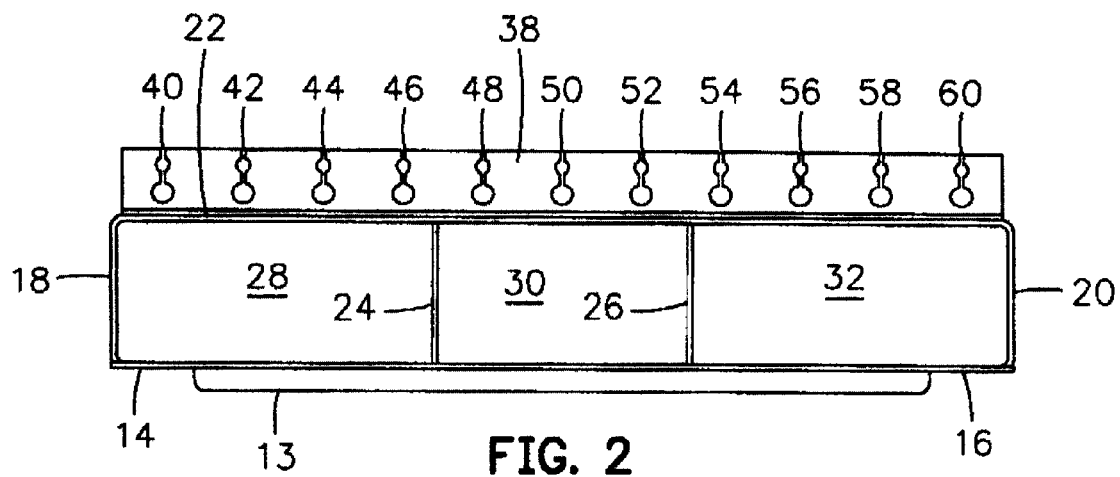
FIG. 2 is a front elevation view of the embodiment of FIG. 1.
Figure 3:
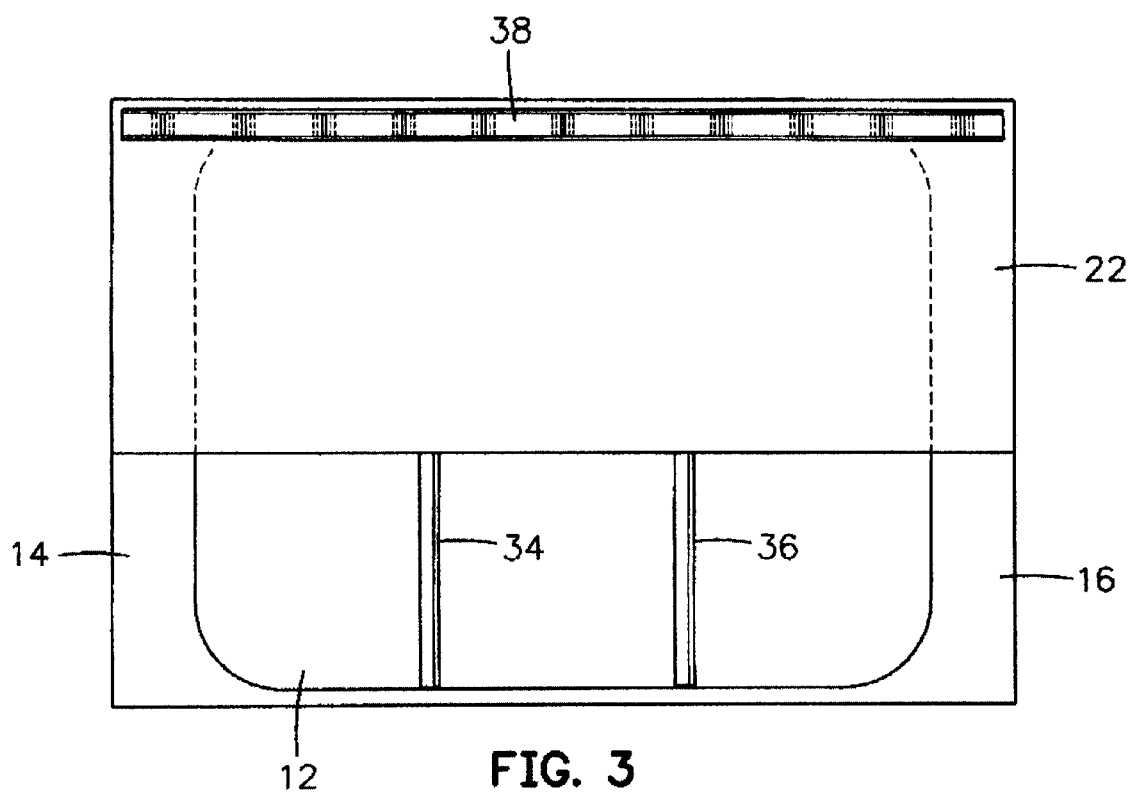
FIG. 3 is a top plan view of the embodiment of FIG. 1.

Referring to FIGS. 1–3 of the drawings, an arthroscopy organizing apparatus or system in accordance with one embodiment of the invention is illustrated and designated generally by the numeral 10. The organizing apparatus, as seen in FIG. 1, has a generally box like primary support structure on a tray which is preferably designed the fit on a MAYO stand or table as shown and will be further explained.

The primary support structure comprises a base support structure in the form of a central tray 12, as shown in FIGS. 2 and 3, adapted to fit a MAYO stand and having extensions 14 and 16 to extend its width beyond that of the width of the MAYO stand to provide greater support area. A box like housing structure having end walls 18 and 20 and a top planar support surface 22 is built on and extends above the tray and forms an open front housing. The box like housing structure is constructed to be about half the depth (fore and aft) of the tray 12 and has an open front to receive instruments. A pair of interior walls or partitions 24 and 26 divide the interior of the housing into three compartments 28, 30 and 32 for receipt and separation of the instruments. A pair of dividers 34 and 36 extend from the ends of the walls across the open tray to the edge thereof to divide the surface thereof into separate support areas.

A line holder and organizer for the system of wires and hoses for the instruments comprises an elongated rail or panel 38 of elastomeric material mounted on top of the housing at or toward the rear thereof. The organizer panel is formed with a plurality of holding slots 40, 42, 44, 46, 48, 50, 52, 54, 56, 58 and 60 for receiving the hoses and lines of the arthroscopy instrument. The slots form adjacent holding members which act to grip the lines and hoses in the slots between them. The slots are each formed with upper and lower holes or rounded portions of different sizes in which the lines and hoses are positioned. The holes are preferably just slightly smaller than the line or hose that is to go therein. This insures that the line will be gripped by the walls of the portion of the slot with sufficient force to be held in place and allow the line or hose to be pulled through.

Figure 6:
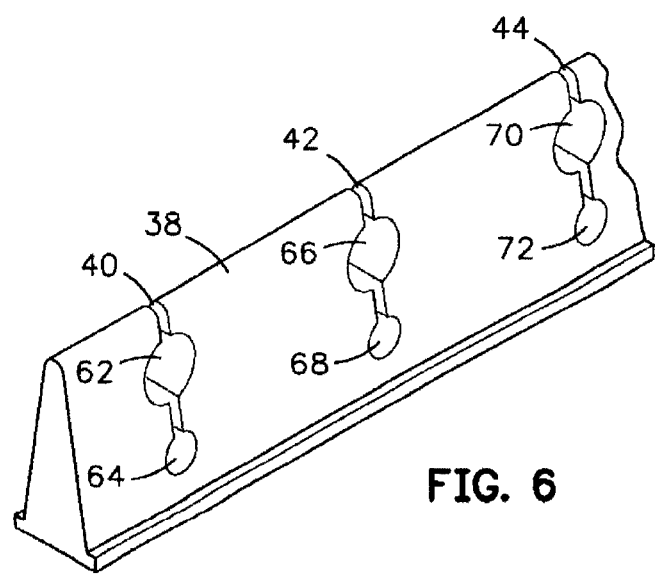
FIG. 6 is a detailed view of a the line holder.

As best seen in FIG. 6, the slots, extend vertically up to and open at the upper edge of the elastic panel. As shown, slots 40, 42, and 44 each have upper and lower holes or enlarged portions 62, 64, 66, 68, 70 and 72 respectively. The holes or enlarged portions of the slots preferably vary in size with a larger at the top and smaller at the bottom to accommodate different size hoses and lines. The elastomeric panel is preferably made from a heat resistant material such as the material currently sold under the mark TEFLON.

The organizer of the present invention is designed to fit on a MAYO stand as illustrated in FIG. 1. A MAYO stand is a standard piece of hospital or operating room equipment which as illustrated has a generally u shaped structural base 74 with wheels or rollers 76 at two rear corners thereof for ease of rolling it about. A telescoping vertical post 78 and 80 is attached to and extends upward from one end of the base such that the base can extend underneath a bed or operating table with the post along one side to hold and adjustably position a table top 82 mounted at the upper end of the post. The telescoping post 78 and 80 is vertically adjustable to position it such that the table top 82 extends over and is adjustably positional above a patient on an operating table. The shelf or table surface 82 is formed with a recess for receiving and holding a tray to prevent it from sliding off. The organizer of the present invention is designed to fit and be supported on a MAYO stand to be accommodated with readily available equipment in an operating room.

Figure 4:
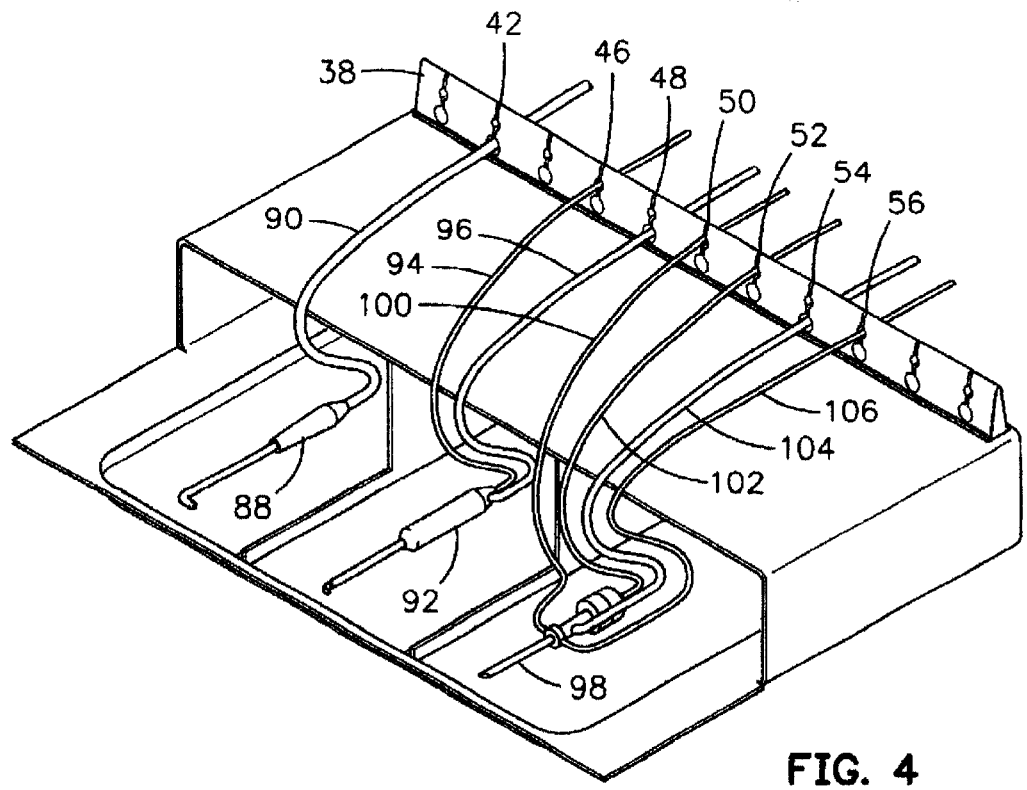
FIG. 4 is a perspective view of the embodiment of FIG. 1 showing instruments in place.

In operation with the present invention, the operating room will be set up with a Mayo stand with a sterilized organizer such as FIG. 4 mounted on the stand such as illustrated in FIG. 1. The sterilized instruments may then be taken to the operating room and removed from their packaging and placed on the tray in a manner such as for example as illustrated in FIG. 4. For example as shown in FIG. 4, a thermo-probe 88 is shown placed in the tray in front of compartment 28 and includes a line 90 extending therefrom and extends through and secured in slot 44 of the holder 38. The line 90 may be positioned in either the upper or lower hole of slot 42 as desired. Preferably the line 90 is positioned such that it is slightly gripped by the slot such that sufficient line can be pulled through to enable the surgeon perform the operation.

A second instrument such as a motorized shaver 92 is shown positioned in the center of the tray in front of center compartment 30 and includes two lines 94 and 96 extending and secured in slots 46 and 48. As discussed previously, only sufficient line is pulled through the holder to enable the surgeon to manipulate the instrument to perform his operation.

A scope and cannula 98 is shown positioned in the tray in front of compartment 32 and includes four lines and hoses extending therefrom. As shown, line 100 extends and is gripped in slot 50, line 102 is in slot 52, line 104 is extended into and gripped in slot 54 and line 106 extends through and is gripped in slot 56. It will be apparent that the line or lines from any one of the instruments may be positioned in any selected desirable slot.

The organizing apparatus of FIGS. 1–4 was designed to provide an optimum size to hold the various instruments needed by the surgeon during the surgery. However, it is desirable that the organizer also be sized to fit a flash autoclave, however this is difficult with the arrangement as illustrated. While the illustrated apparatus will fit a flash autoclave when all shelves and racks are removed from the autoclave such is not desirable because of the inconvenience.

Figure 5:
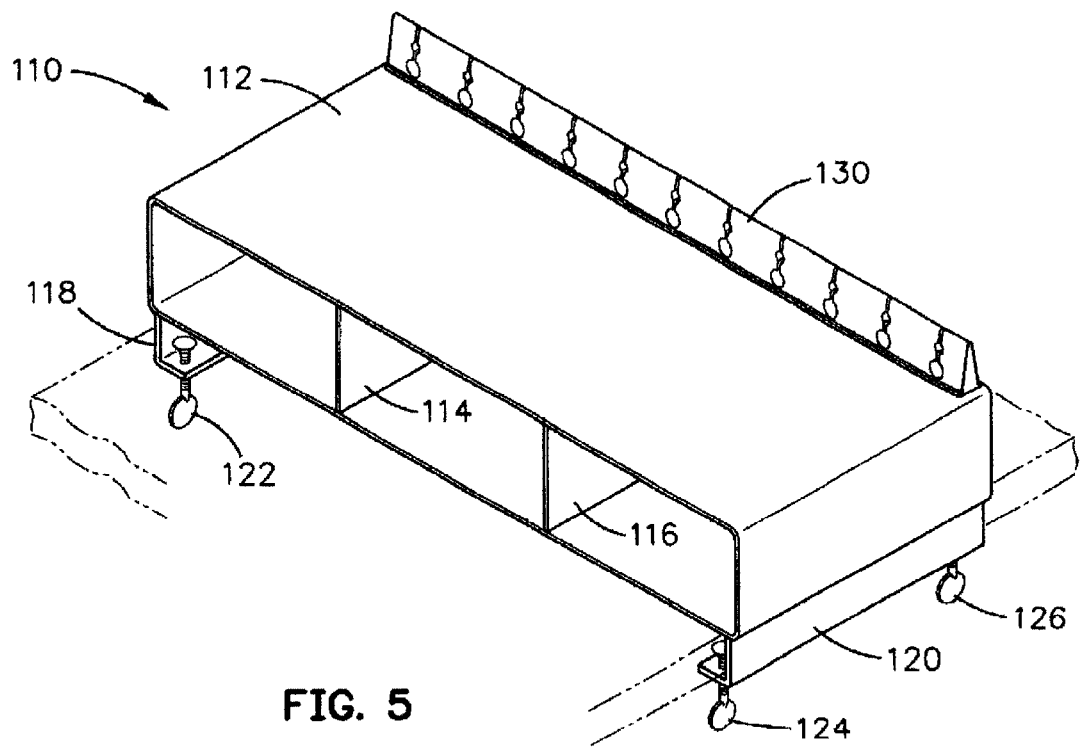
FIG. 5 is a view like FIG. 4 another embodiment of the invention.

Referring to FIG. 5, another embodiment of apparatus in accordance with the invention is illustrated which is designed to be sized to fit the flash autoclave yet clamp to the typical MAYO stand. As illustrated, the apparatus designed generally by the numeral 110 comprises an elongated box like housing structure 112 substantially as in the previous embodiment however without the laterally extended tray as in the prior embodiment. The embodiment includes the box like structure with partitions 114 and 116 dividing the interior thereof into three compartments as in the prior embodiment. The housing forms a bridge like structure that is provided with a pair of clamps 118 and 120 designed to fit over the edges of the shelf or table of a MAYO stand and include clamping means such as thumbscrews 122, 124 and 126 for securing it to the MAYO stand or table. Other suitable clamping means may be utilized or provided. The apparatus is provided with a slotted line holder 130 as in the previous embodiment. This line holder has the usual series of slots with different size openings as in the prior embodiment.

Figure 7:
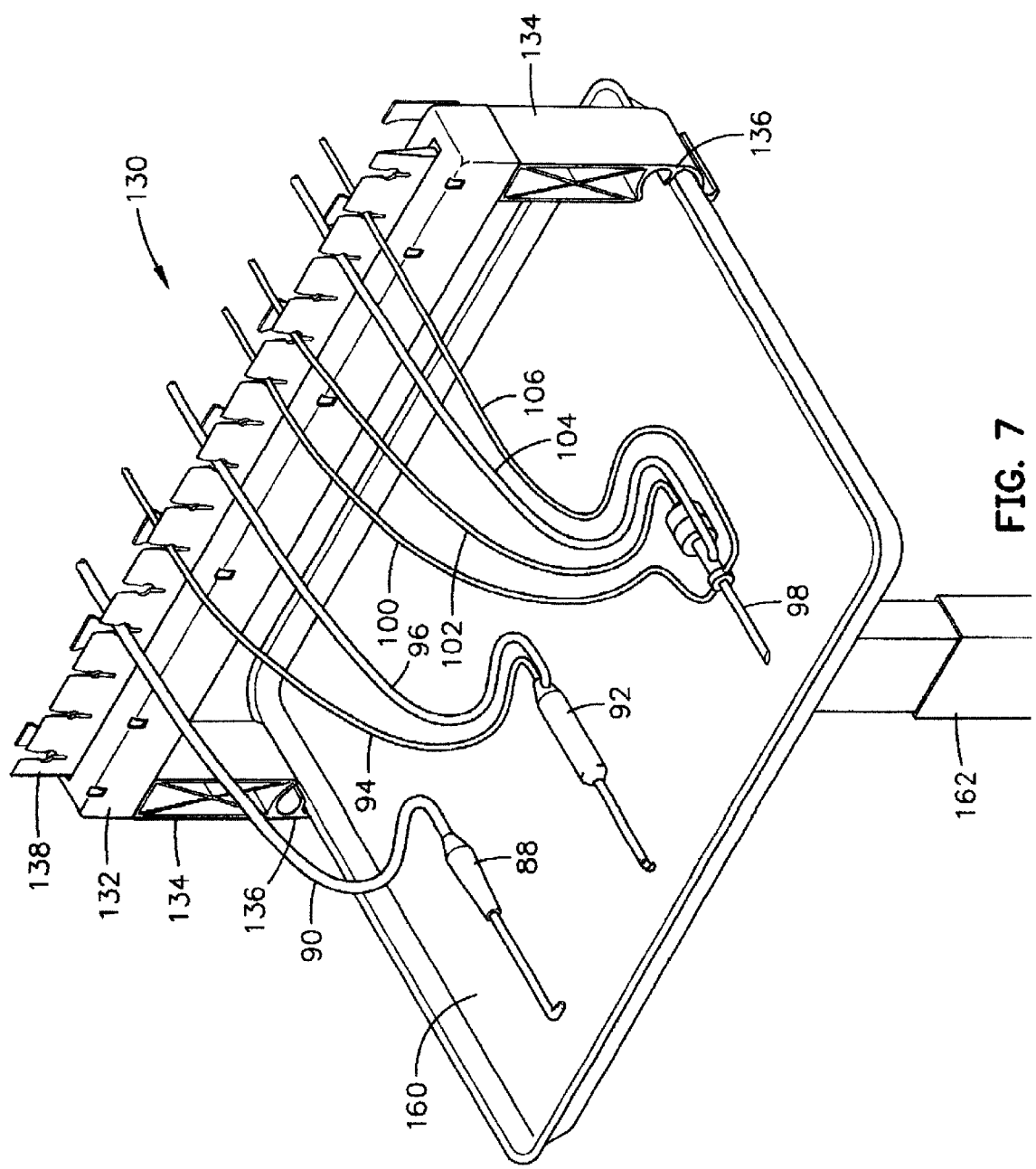
FIG. 7 is a view like FIG. 4 of a further embodiment of the invention.

Referring to FIG. 7, a further embodiment of an apparatus in accordance with the invention is illustrated which is constructed and configured to span and clamp to the side edges of a support table such as a typical MAYO stand. As illustrated, the apparatus designated generally by the numeral 130 comprises an elongated substantially rigid box-beam or bridge like structure 132 that spans a support table substantially as in the previous embodiment. The bridge like structure is provided with a pair of downwardly depending legs 134 that detachably attach to the beam and detachably attach such as by clamping to a tray or support table. The legs may be made integral with the beam or may be attached by hinges or other means. The legs support the bridge-like structure above the support table providing space underneath for tools and instruments. Each leg is formed with a clamp structure 136 at one end thereof formed integral therewith. The clamps are designed with a curved surface to fit over or around to engage and grip or clamp to opposite side edges of a tray or top of a table or stand such as a MAYO stand, and detachably secure the organizing apparatus to the MAYO stand or table. As shown, the clamp device is illustrated as having two different sizes of clamp opening which can receive and fit the most common employed stands or tables. The clamps depicted are illustrative only and other suitable clamping means may be utilized or provided.

The organizing apparatus is provided with a slotted line holder 138 as in the previous embodiment. This line holder is preferably formed of an elastomeric material and has the usual series of slots with different size openings to receive different size lines as in the prior embodiment. It should be appreciated that the line holder may be integral with the beam and have yieldable members or fingers forming the slots with configuration or design. A slot or recess 140 is formed in the top of the beam or bridge like structure 132 to receive and mount the line holder. The line holder has elastomeric pins or projections that extend into holes in the beam and secure the holder in place.

Figure 8:
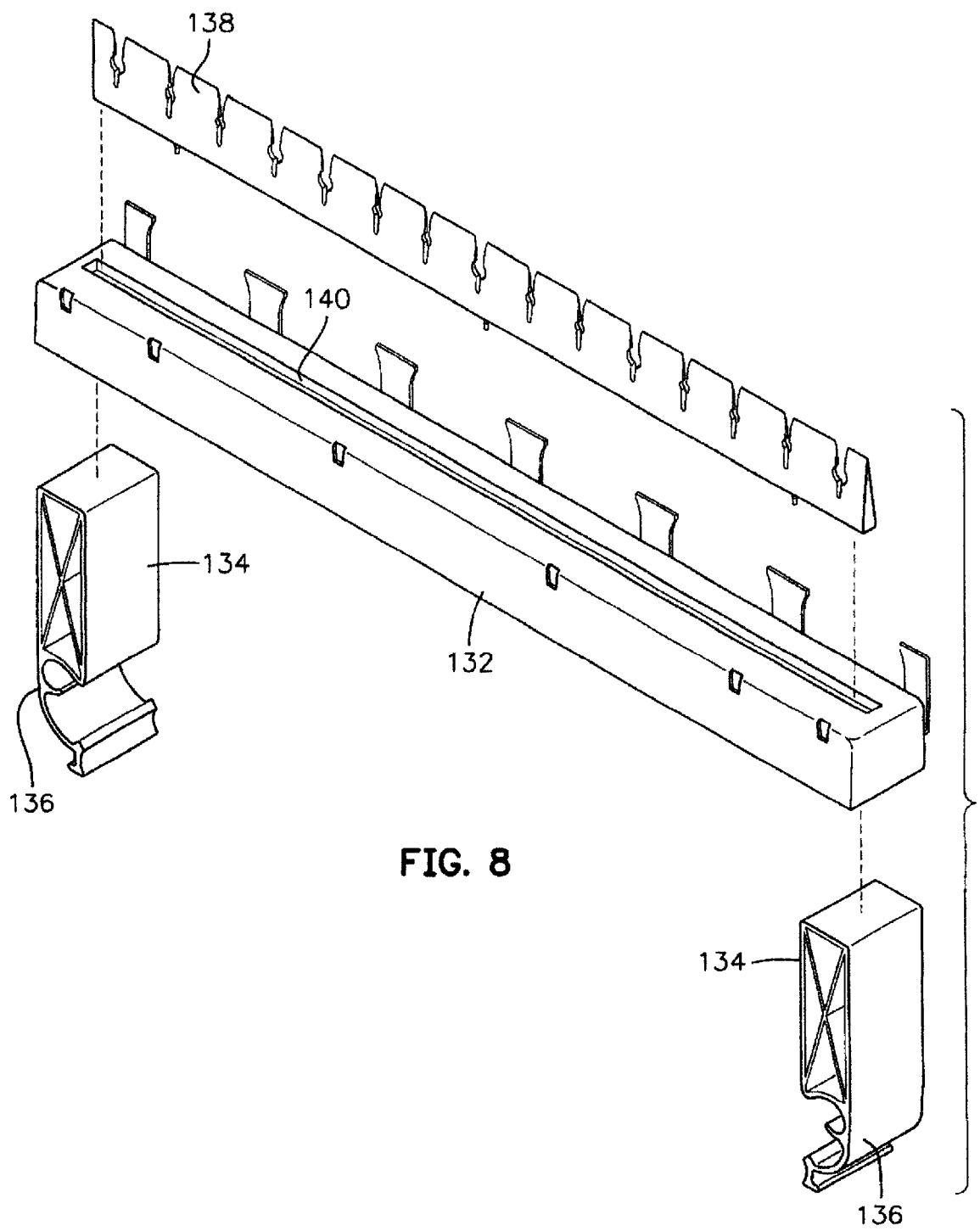
FIG. 8 is a front exploded isometric view of the embodiment of FIG. 7.
Figure 9:
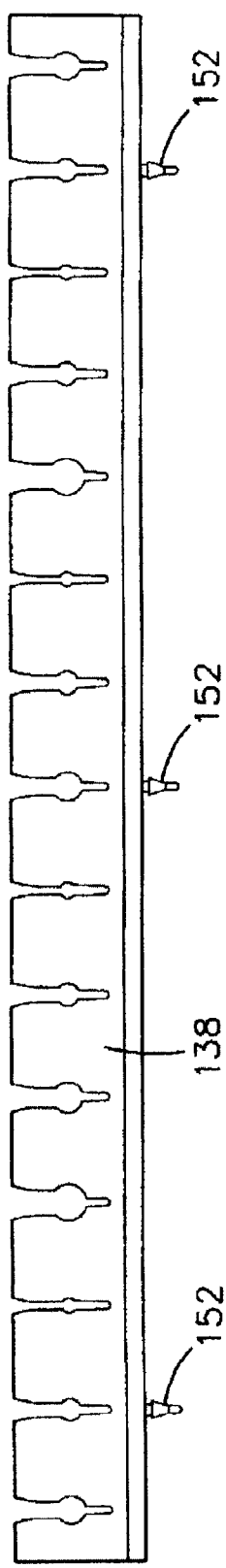
FIG. 9 is a front elevation view of the line holder of the embodiment of FIG. 7.

As best illustrated in FIG. 8, the organizer apparatus is of a knock down modular construction that is easily assembled and disassembled. The bridge-like structure 132 is a thin wall box-like construction and is preferably molded from a suitable plastic material such as polypropylene or the like. It is apparent however, that it could be constructed having a like or similar structure from any suitable sheet metal including but not limited to stainless steel and aluminum.

Figure 10:
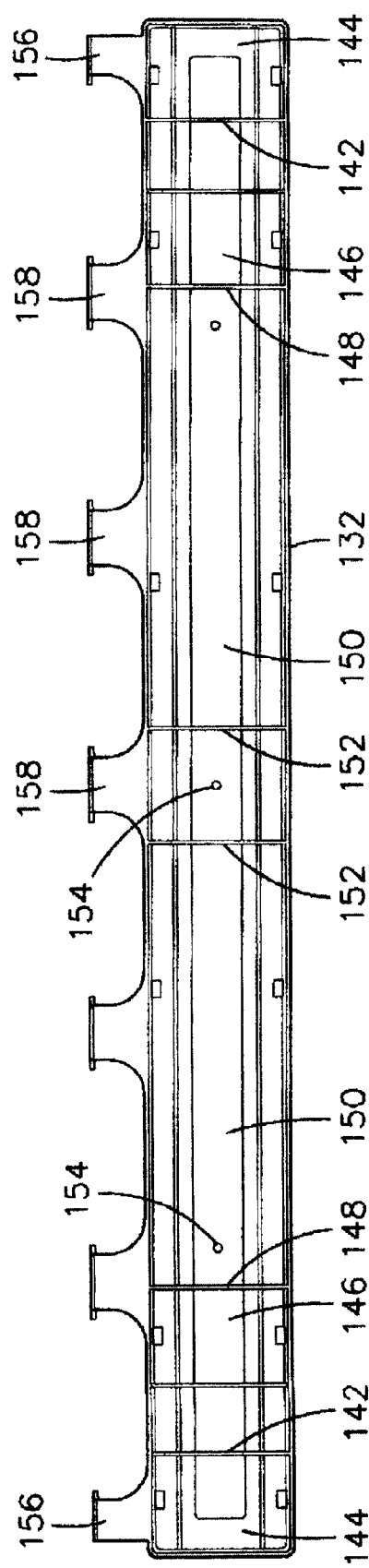
FIG. 10 is a bottom plan view of the embodiment of FIG. 7.

The bridge-like structure or beam is constructed with an open bottom as shown in FIG. 10 with partitions 142 adjacent each end, forming sockets 144 for detachably receiving the upper end of the legs 134 for assembly as shown in FIG. 7. These sockets are positioned to enable the assembly to span the lengthwise or long dimension of a tray or table. Additional sockets 146 are formed by additional partitions for receipt of the legs to provide an assembly that spans the width of a tray or table. A pair of receptacles 150 are formed by partitions 148 near the ends and partitions 152 near the center to receive and stow the legs for making the assembly compact when broken down for ease of shipping. The line holder 138 is formed with a plurality of nipples or extensions 152 that are formed with a tapered portion and shoulders as illustrated so that when extended into holes 154 the line holder is held in place.

The beam is preferably formed with a plurality of hooks along one side such as 156 at the ends and 158 intermediate the ends. These hooks may be used to store line until ready for use or to stow excess line by looping line around a respective hook. Additional line may be thereby held until connected to equipment or stowed out of the way of the surgeon when not needed.

It is apparent that the apparatus of the present invention can be made from many different materials. For example, stainless steel is a preferred material for the organizer unit for re-useable units. However, it can be made by molding from any one of several known disposable medical grade plastic materials.

Referring to FIG. 7, a unit in use is illustrated. The unit is attached by clamping to the edges of a tray of a tray table or stand. The tray or support surface is mounted on a vertically adjustable vertical support 162. In operation a plurality of instruments as illustrated in FIG. 4 is shown with the same elements designated by the same numerals. The tools or instruments are shown supported on the support surface of the tray 160.

While I have illustrated and described my invention by means of a number of specific embodiments, it is to be understood that numerous changes and modifications may be made therein without departing from the spirit and the scope of the invention as shown in the appended claims.

I claim:

1. An organizing apparatus for medical instruments comprising:
   an elongated support member having opposite ends and releasable attachment members secured to and depending downward from said opposite ends, each attachment member having clamp means with a surface defining at least one clamp opening for receiving and engaging a side edge of a substantially planar support member, the clamp means adapted for detachable attachment of said elongated support member to opposite side edges of a substantially planar support member; and
   an elongated line holder mounted on said support member and having a plurality of resilient holding members defining line receiving and holding areas between adjacent holding members.

2. An organizing apparatus according to claim 1 wherein:
   said elongated support member comprises a box beam having at least one socket proximate each end; and
   said releasable attachment members are on legs that detachably mount in said sockets.

3. An organizing apparatus according to claim 2 wherein said line holder comprises a resilient elastomeric panel member divided by a plurality of slots into said holding members.

4. An organizing apparatus according to claim 3 wherein at least some of said slots have enlarged areas therein.

5. An organizing apparatus according to claim 2 wherein:
   said elongated support member comprises a box beam having a plurality of sockets proximate each end; and
   said releasable attachment members are on legs that detachably mount in said sockets.

6. An organizing apparatus according to claim 2, wherein said support member has a recess for receiving and stowing each of said legs.

7. An organizing apparatus according to claim 1 wherein said line holder comprises a resilient elastomeric panel member divided by a plurality of slots into said holding members.

8. An organizing apparatus according to claim 7 wherein at least some of said slots have enlarged areas therein.

9. An organizing apparatus according to claim 1 wherein said line receiving and holding areas comprises a plurality of slots in a resilient elastomeric panel.

10. An organizing apparatus for medical instruments comprising:
    an elongated substantially rigid support member having opposite ends;
    a releasable attachment member secured to and depending downward from each of said opposite ends for detachable attachment of said support member to opposite side edges of a substantially planar support member, each attachment member having a clamp with at least one opening defined by a curved surface adapted for receiving and engaging a side edge of a substantially planar support member; and
    an elongated line holder mounted on a top surface of said elongated support member and having a plurality of resilient holding members defining line receiving and holding areas between adjacent holding members.

11. An organizing apparatus according to claim 10 wherein said clamps have multiple openings of different sizes and are adapted to mount on different thickness side edges of a table.

12. An organizing apparatus according to claim 10 wherein:
    said elongated support member comprises a box beam having at least one socket proximate each end; and
    said releasable attachment members are on legs that detachably mount in said sockets.

13. An organizing apparatus according to claim 12 wherein said line holder comprises a resilient elastomeric panel member divided by a plurality of slots into said holding members.

14. An organizing apparatus comprising:
    an elongated substantially rigid support member having opposite ends;
    a releasable attachment member secured at an inner end to and depending downward from each of said opposite ends and including clamping means at an outer end for detachable attachment of said elongated support member to opposite side edges of a substantially planar support member, each clamping means having at least one opening defined by a curved surface adapted for receiving and engaging a side edge of a substantially planar support member; and
    an elongated line holder comprising a resilient elastomeric panel member divided by a plurality of slots defining line receiving and holding areas mounted on a top surface of said support member.

15. An organizing apparatus according to claim 14 wherein said clamp means have a plurality of different size openings for receiving and attaching said elongated support member to the side edges of different thickness tray tables.

16. An organizing apparatus according to claim 14 wherein:
   said elongated support member comprises a box beam having at least one socket proximate each end; and
   said releasable attachment members are on legs that detachably mount in said sockets.

17. An organizing apparatus according to claim 16 wherein:
   said elongated support member comprises a box beam having a plurality of sockets proximate each end; and
   said releasable attachment members are on legs that detachably mount in said sockets.

18. An organizing apparatus according to claim 17, wherein said beam has a recess for receiving and stowing each of said legs.

19. An organizing apparatus according to claim 14 wherein at least some of said slots have enlarged areas therein.

20. An organizing apparatus according to claim 19 wherein at least some of said slots have different size enlarged areas therein.

* * * * *